US012599721B2

(12) United States Patent
Hirschel et al.

(10) Patent No.:  US 12,599,721 B2
(45) Date of Patent:      Apr. 14, 2026

(54) CARTRIDGE FIXATION FOR A DRUG DELIVERY DEVICE

(71) Applicant: Ypsomed AG, Burgdorf (CH)

(72) Inventors: Jürg Hirschel, Bern (CH); Marcel Allenspach, Burgdorf (CH); Manuel Mosimann, Burgdorf (CH); Gabriel Kalbermatter, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 1045 days.

(21) Appl. No.: 17/713,447

(22) Filed: Apr. 5, 2022

(65) Prior Publication Data

US 2022/0233777 A1      Jul. 28, 2022

Related U.S. Application Data

(63) Continuation of application No. PCT/EP2020/078700, filed on Oct. 13, 2020.

(30) Foreign Application Priority Data

Oct. 15, 2019    (EP) ..................................... 19203413

(51) Int. Cl.
    *A61M 5/24*        (2006.01)
    *A61M 5/315*        (2006.01)
(52) U.S. Cl.
    CPC .............. *A61M 5/24* (2013.01); *A61M 5/315* (2013.01); *A61M 2005/2407* (2013.01);
    (Continued)

(58) Field of Classification Search
    CPC .................... A61M 5/24; A61M 5/315; A61M 2005/2407; A61M 2005/2477; A61M 2005/2492
    See application file for complete search history.

(56) References Cited

U.S. PATENT DOCUMENTS 9,132,237 B2 *  9/2015  Harms .............. A61M 5/31585
9,149,580 B2    10/2015  Jugl et al.
(Continued)

FOREIGN PATENT DOCUMENTS

EP          3808393 A1      4/2021
WO      2021074105 A1      4/2021

OTHER PUBLICATIONS

Extended European Search Report issued in European Patent Application No. 19203413.0 issued on Jan. 8, 2020, 9 pages.
(Continued)

*Primary Examiner* — Dung T Ulsh
(74) *Attorney, Agent, or Firm* — Dorsey & Whitney LLP

(57) ABSTRACT

A housing for a drug delivery device for administrating a liquid drug from a cartridge includes a recess for accommodating a proximal portion of the cartridge and a deformable member arranged inside the recess. The deformable member includes a proximal end attached to the housing and a distal end movable within the recess. The deformable member is deformable from a non-deformed state to a deformed state by a displacement of the distal end. In the deformed state the deformable member is adapted to limit a movement of a cartridge in the longitudinal direction relative to the housing. The deformable member further includes an arch, and in the deformed state the arch is deformed both elastically and plastically.

19 Claims, 4 Drawing Sheets

(52) U.S. Cl.
CPC .............. *A61M 2005/2477* (2013.01); *A61M*
*2005/2492* (2013.01); *A61M 2207/00*
(2013.01)

(56) References Cited

U.S. PATENT DOCUMENTS

| | | | |
|---|---|---|---|
| 9,867,945 B2 | 1/2018 | Nzike et al. | |
| 2007/0021718 A1* | 1/2007 | Burren ................. | G01F 11/027 |
| | | | 604/110 |
| 2012/0172818 A1* | 7/2012 | Harms ............. | A61M 5/31585 |
| | | | 604/230 |
| 2013/0006193 A1 | 1/2013 | Veasey et al. | |
| 2016/0193414 A1 | 7/2016 | Mcloughlin et al. | |
| 2017/0348489 A1* | 12/2017 | Hirschel ................. | A61M 5/24 |

OTHER PUBLICATIONS

International Search Report and Written Opinion issued in International Application No. PCT/EP2020/078700, issued on Oct. 30, 2020, 10 pages.

* cited by examiner

CARTRIDGE FIXATION FOR A DRUG DELIVERY DEVICE

CROSS REFERENCES TO RELATED APPLICATIONS

This application claims priority to International Patent Application No. PCT/EP2020/078700, filed Oct. 13, 2020, entitled "CARTRIDGE FIXATION FOR A DRUG DELIVERY DEVICE," which claims priority to European Application No. 19203413.0, filed Oct. 15, 2019, entitled "CARTRIDGE FIXATION FOR A DRUG DELIVERY DEVICE", each of which is incorporated by reference herein, in their entirety and for all purposes.

TECHNICAL FIELD

Disclosed are medicament delivery devices for delivering, administering, dispensing, injecting, or infusing substances and/or liquids such as insulin or hormone preparations that include a housing and a cartridge holder connectable to the housing for holding a cartridge within the housing and the cartridge holder.

BACKGROUND

A variety of diseases exist that require regular treatment by parenteral subcutaneous or intramuscular administration of a drug or medicament, and a number of drug delivery devices have been developed to support a patient in accurately and controllably delivering an amount of drug in a self-administration process.

Injection devices for self-administration typically include a dosing and dispensing mechanism allowing a user to dial a desired dose and subsequently administer or dispense the dialed dose. The dispensing mechanism includes a piston rod, which is movable relative to a housing of the injection device. The piston rod is adapted to move a plug inside the cartridge in a distal direction in order to dispense the drug through a distal opening of the cartridge.

Such an injection device further includes the cartridge containing the liquid drug or medicament. The cartridge is usually held by a cartridge holder and a housing of the injection device accommodating the dose and dispensing mechanism. To hold the cartridge, a distal portion of the cartridge is accommodated in the sleeve-shaped cartridge holder and a proximal portion of the cartridge is accommodated in a recess of the housing. During assembly, the cartridge is either first inserted with its proximal portion in the recess of the housing or it is first inserted with its distal portion in the cartridge holder. Subsequently, the cartridge holder is connected with its proximal end with a distal end of the housing. For dosing and dispensing accuracy, it is important to rigidly and precisely hold the cartridge relative to the housing and the piston rod, in particular in an axial or dispensing direction.

Means for holding the cartridge within a housing are known in the art. For example, U.S. Pat. 9,867,945 B2 discloses a cartridge holder having inwardly and outwardly movable tongues on a proximal portion of the holder. The movable tongues include an inwardly directed protrusion adapted to engage with a proximal rim portion of the cartridge. During insertion of the cartridge into the holder the tongues elastically bend outwards and flex back when the cartridge is inserted. Accordingly, in an assembled state, the cartridge may be clamped between a distal end stop face of the holder and the protrusions such that the cartridge is secured against distal and proximal displacement with respect to the cartridge holder.

U.S. Pat. No. 9,149,580 B2 discloses a cartridge holder including a tensioning member connected to a compression spring positioned at a shoulder portion of a bottle-necked body of a cartridge. The cartridge holder is further equipped with at least one counter-bearing element adapted to provide a proximal end stop for the cartridge. Therefore, the cartridge can be effectively clamped between the tensioning member and the counter bearing element.

US 2007/0021718 A1 discloses holding means for a cartridge including a spring inserted into a recess of a housing of a pen injector. A proximal end of the spring is held by a snap-fit connection in a bottom of the recess. When a cartridge is inserted with its proximal portion into the recess the spring is compressed. In the assembled state, the compressed spring holds and biases the cartridge to a distal inner wall of the cartridge holder. The cartridge is thus axially held relative to the housing and the cartridge holder.

These prior art approaches suffer from the fact that the holding means for holding the cartridge relative to the housing may exert a biasing force or holding force to the cartridge when inserting the cartridge into the housing which may unintentionally increase. Such a high holding force may occur if the cartridge is longer than expected (e.g., due to manufacturing tolerances) or if the cartridge is inserted during assembly too deeply into the housing and thus the biasing element is overly compressed. If the holding force is too high the cartridge may be damaged or even break. On the other hand, if the holding force is too low the cartridge may move within the housing, such as after a storage period when material relaxation has been occurred.

SUMMARY

It is thus an objective of the present disclosure to reliably and precisely hold the cartridge relative to a housing of the drug delivery device or, more generally, to provide an easy to manufacture alternative holding means with improved assembling capabilities.

This objective is achieved by providing a housing for a cartridge unit for a drug delivery device according to the disclosure and claims.

According to certain implementations, a housing for a drug delivery device for administrating a liquid drug from a cartridge may include a recess for accommodating at least a proximal portion of the cartridge. The recess has an axis defining a longitudinal direction. The housing may further include a deformable member arranged inside the recess, where the deformable member may include a proximal end attached to the housing, such as to a sidewall of the recess, and a distal end movable within the recess relative to the housing and relative to the sidewall. The deformable member may deformable from a non-deformed state or an initial state to a deformed state by a displacement of its distal end. In the deformed state the deformable member may be adapted to limit a movement, such as a proximal movement, of a cartridge that may be present in the recess in the longitudinal direction relative to the housing. The deformable member may include a first arch between the proximal end and the distal end in the non-deformed state and in the deformed state. In the deformed state, the first arch may be deformed both elastically and plastically.

During assembly, the cartridge may be inserted into the drug delivery device, and a proximal portion of the cartridge may be inserted into the recess of the housing of the drug delivery device. During insertion of the cartridge into the housing recess, the deformable member may be deformed from the non-deformed state to the deformed state. The deformable member may be deformable by a displacement of the distal end. This distal end may be displaced by a proximal end of the cartridge when the cartridge is inserted into the housing recess. When the cartridge has been inserted into a final axial position into the housing recess, the arch of the deformable member may be elastically deformed and at the same time plastically deformed. In this deformed state, the housing with the deformable member may be adapted to limit a movement of the cartridge relative to the housing in the proximal, longitudinal direction. Additionally, if the cartridge is inserted into its final axial position the deformable member together with a cartridge holder or with any counter element connected to a distal end of the housing may be adapted to hold the cartridge relative to housing such that the cartridge is prevented from further movement relative to the housing.

During insertion of the cartridge, a resisting force or reaction force exerted by the deformed deformable member may act on the proximal end, such as on a rim portion, of the cartridge. There may be no resisting force in the non-deformed state when the cartridge does not abut the deformable member. The force initiates and may continuously increase at least in a first part during insertion of the cartridge into the recess because the arch of the deformable member may be deforming and some portions of the deformable member may be compressed. When the insertion of the cartridge is complete and the deformable member is in its deformed state there may still be a force exerted by the deformable member acting on the cartridge because the deformable member is in the deformed state not only plastically deformed but also elastically deformed.

The deformable member may be adapted to limit a movement of the cartridge in the recess in the longitudinal direction relative to the housing. Therefore, the cartridge may be held in the housing in a predefined, final axial position or in a predefined final axial positional range in the recess. Due to the arch-shaped member the force progression in relation to the deflection or to the deforming path during deformation of the arch may be optimally configured. For example, the arch may be configured such that the force progression is nearly linear or such that it follows a suitable mathematic function. Thus, the force acting on the cartridge may be predictable. Therefore, the deformable member may be adapted to reliably limit the axial movement of an inserted cartridge. In the assembled state, when a counter element, for example a cartridge holder, is mounted to the housing the cartridge may be reliably and precisely held such that the cartridge is secured against distal and proximal displacement.

Since the force acting on the cartridge may be adjustable by configuring the deformable member with an arch, the inserted cartridge may be held with a predefined force within a predefined force range. This may provide the ability to hold cartridges with different lengths, which may be caused due to manufacturing tolerances. Hence, the arch may be configured such that a short as well as a long cartridge may be optimally held by the deformable member relative to the housing.

The elastic deformation of the arch may cause a force acting on the proximal end of the inserted cartridge in a distal and longitudinal direction. The deformed arch may bias the cartridge in a distal direction against a stop element in a cartridge holder or against any counter element in an assembled state.

During storage, material relaxation may occur. Due to the elastic deformation of the arch there may still be a remaining force acting on the cartridge and a movement of the cartridge may be reliably limited even if the initial force is reduced due to any such material relaxation.

Besides the elastic deformation, the deformable member may be further plastically deformed in the deformed state such that a further movement of the cartridge may limited by the deformable member. The effect of the plastic deformation may be that, depending on the configuration of the arch, the exerted force on the cartridge by the member may be limited to a specific maximum value. Thus, the plastic deformation of the deformable member may limit the exerted (reaction) force acting on the cartridge and may thus prevent damage or even breakage of the cartridge.

In an assembled state when a holding means (e.g., a cartridge holder) is mounted the cartridge may be prevented from movement or the cartridge may only move in a very restricted range (e.g., several micrometers) relative to the housing and relative to any dosing element such as a plunger rod accommodated in the housing. Thus, the accuracy of the dosing and dispensing may be ensured.

In certain implementations, a sleeve shaped cartridge holder may include a recess adapted to accommodate a distal portion of the cartridge and may be mounted to the housing for completion of mounting of the cartridge into the drug delivery device. For instance, the opening of the recess of the cartridge holder may be configured to slide over a distal end of the cartridge. The cartridge may, as previously described, have its proximal end inserted into the housing. Alternatively, the cartridge may first be inserted with its distal portion in the cartridge holder and then the proximal portion of the cartridge may be inserted into the housing as described previously. In both variants, the proximal end of the cartridge holder may then be fixed to the distal end of the housing, for example, by a snap fit connection. The cartridge may thus be held by the cartridge holder and the housing relative to the housing inside the drug delivery device.

The term "plastic deformation" means that the deformation is irreversible and thus the deformation stays even after removal of the applied force. The term "elastic deformation" means that the deformation is recoverable as it disappears after the removal of the applied force.

The term "arch" means that the member has a curved shape between the proximal end and the distal end. The arch or the curved shape may form an arc of, for example, ranging between 30° to 190°, such as between 70° and 120°. The arch may be directed in any direction. The deformable member may include one or more arches between the two ends.

In the deformed state, the deformable member may be adapted to limit a movement of the cartridge in the longitudinal direction. That means movement of the cartridge may not be stopped or blocked in any case, but a restricted movement of the cartridge may only be possible. For example, the insertion force required for a movement of the cartridge in the proximal direction may be higher than in the non-deformed state.

The term "non-deformed state" means the deformable member is in its initial state after the manufacturing. The arch or any other portion of the deformable member is not yet deformed by a user or by an assembly process, such as by an insertion of the cartridge into the housing. The distal end of the member may not be moved from its initial position.

In contrast, the term "deformed state" means at least a section of the deformable member, such as the shape of the arch has been altered from an initial shape to a new shape. In the deformed state the distal end of the deformable member may be moved away from its initial position, for example, from a distal position to a proximal position relative to the housing. The term "deformed state" is not limited to a specific deformation of the arch but the deformed state includes all positions and orientations of the deformable member and of the arch that is different from their initial positions and in the deformed state the arch is deformed both elastically and plastically. In order to fulfill this limitation the deformation of the material of the deformable member must be in the so-called strain hardening region of the stress-strain curve of the material. That means the deformable member is in the deformed state as soon as the deformation of the material exceeds the pure (linear) elastic region and an irreversible plastic deformation occurs.

In the present context, the terms "substance", "drug", "medicament" and "medication" are to be understood to include any flowable medical formulation suitable for controlled administration through a means such as, for example, a cannula or a hollow needle, and includes a liquid, a solution, a gel or a fine suspension containing one or more medical active ingredients. A medicament may be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances The term "distal" is meant to refer to the direction or the end of the drug delivery device carrying an injection needle or an injection cannula, whereas the term "proximal" is meant to refer to the opposite direction or end pointing away from the needle or cannula.

The term "injection system" or "injector" refers to a device that is removed from the injection site after each medication event or drug delivery process, whereas the term "infusion system" refers to a device with a cannula or needle that remains in the skin of the patient for a prolonged period of time, for example, several hours.

In certain implementations, the deformable member is arm-shaped and the arch of the deformable member may be located between the proximal end and distal end of the arm-shaped member. The term "arm-shaped" means the member has preferably a longitudinal shape or form between the proximal end and the distal end of the member. Hence, the length is longer than the width of the member. However, the arm-shaped member must not be extending along the longitudinal direction of the housing but it may extend along any other direction or the whole member can have a curved form, which does not extend along a specific direction. The arm-shaped member enables configuration of an advantageous force procession of the force acting on the cartridge when the cartridge is inserted into the housing. Furthermore, the arm-shape may allow for an efficient production of the deformable member. Where the deformable member is made of plastic, the arm-shape may be easy to demold or remove from an injection molding tool.

The deformable member may be deformable in the area of the arch. However, during deformation from the non-deformed state to the deformed state, other portions of the member may also be deformed.

The deformable member may be deformable from the non-deformed state to the deformed state by a displacement of the distal end of the member in the longitudinal direction relative to the housing, such as by a proximal displacement. The displacement may be caused when the cartridge is inserted into the recess of the housing with its proximal portion and moved in the proximal direction parallel to the longitudinal axis. That means, during insertion of the cartridge along the longitudinal direction the distal end of the member may also be moved substantially along the longitudinal direction. This may allow for an easy and quick deformation of the deformable member and may thus allow for an easy and quick limitation of a movement of the cartridge relative to the housing.

Alternatively, the deformable member may be deformable from the non-deformed state to the deformed state by moving the distal end in a direction perpendicular to the longitudinal direction or in any other direction.

In certain implementations, the distance between the proximal end and the distal end of the deformable member defines a length of the member in the longitudinal direction, where in the deformed state, the length is reduced compared to the non-deformed state. For instance, the deformable member such as the arch may be bent or deformed such that the length of the deformable member is reduced during deformation. Due to the deformation at least a portion of the arch may be compressed and/or stretched. The strain of the material due to the deformation may cause a force acting at least partially in the longitudinal direction and may thus be adapted to bias the inserted cartridge against a cartridge holder or any counter element at a distal end of the cartridge in an assembled state.

Alternatively, the length of the member may be enlarged in the deformed state compared to the non-deformed state. This may occur, for example, if the arch of the member is stretched during deformation.

In some examples, in the deformed state a first portion of the arch may be elongated and a second portion of the arch may be compressed compared to the non-deformed state. Hence, the arch may be deformed in such a way that an initial curve of the arch may be further bent. For example, an inner radius defining an inner curvature of the arch may be decreased in the deformed state compared to the non-deformed shape. Such a deformation may allow for a space-saving configuration of the deformable member. Furthermore, such a deformation may allow for a continuous and predicable force progression in relation to the deforming path.

Alternatively, the arch may be deformed in any other way, such as a deformation only by elongation or only by compression.

The deformable member may include a second arch between the proximal end and the distal end, and the previously described first arch and the second arch may constitute an s-shaped form in the non-deformed state and in the deformed state. The term "s-shaped" means the deformable member has more or less of an s-form. That means the first arch is preferably arranged adjacent to the second arch along a continuous line of the form of the deformable member. The two arches of the deformable member may not need to exactly and completely form an s-curve. The s-shape form may allow for a further compact design. In the s-shaped member strain and stress within the body of the member may be advantageously and widely dispersed within the body of the member and thus local strain peaks and local stress peaks may be avoided. Furthermore, during deformation the s-shape form of the deformable member may allow for a continuous and optimal force progression in relation the deflection of the member.

The second arch may allow for a configuration of the deformable member such that the resisting force or holding force of the deformable member during its deformation may be smooth, continuous and may be held in an optimal range. Namely, the force in relation to the deflection (deforming path) of the s-shaped member may in a first section rapidly increase and in a second section be very low or almost constant. The almost constant section may be desirable because a cartridge with a minimum length and a cartridge with a maximum length of a tolerance range may be held with almost the same predetermined force.

The deformable member may be deformable in the first and the second arch, such as exclusively deformable in the first and the second arch. The portions of the deformable member not belonging to the first or second arch may thus not be deformed. Therefore, during deformation from the non-deformed state to the deformed state only the first arch and the second may be deformed and the rest of the deformable member may not be deformed, and may be unable to be deformed.

In an alternative embodiment the deformable member may be configured such that only one of the two or more arches is deformed and the other arches may not be deformed in the deformed state of the deformable member.

A plane area of the cross-section of the deformable member may vary between the proximal end and the distal end. The plane area of the cross-section lies in a plane perpendicular to the center line of the deformable member. In some implementations, the deformable member may be tapered or the deformable member may include tapered portions. The varying plane area of the cross-section may permit the location of the deformable arch portion to be optimally defined. Hence, the plane area in the deformable portion in the arch may be reduced compared with the non-deformable portion of the deformable member such that the location of the deformation may be precisely defined and predicable. Furthermore, the plane area in the deformable portion may be configured such that the deformable portion is easily and optimally deformable.

In some implementations, the deformable member may be unitarily formed with the housing. The deformable member may be formed in one piece and for instance by the same material as the housing. This may allow for an efficient production of the housing with the deformable member.

The deformable member may be a separate and single part, which may be connected, for example, by bonding, e.g., an adhesive bond, or by a snap-fit connection.

The deformable member may be made of a polymer such as a polyoxymethylene, polypropylene, polyethylene, poly-carbonate-acrylonitrile-butadiene-styrene, polybutylentere-phthalate, a polyester or a polyamide. These polymers, such as polyethylene, may be easily deformable and may have an advantageous value for the elongation at break. That means the deformable member may be deformed both plastically and elastically in a specific deformation range without risk of breakage. For instance, polypropylene is very ductile, which means the deformable member is easy to stretch or easy to deform.

According to certain implementations, the housing may include at least two deformable members and may be arranged inside the recess of the housing. The two or more members may be arranged circumferentially and may be spaced apart evenly and/or symmetrically from each other.

Thus an insertion movement of a cartridge into the recess of the housing may be limited by two or more deformable members and the insertion movement may thus be limited in a safe and optimal manner.

The proximal end of the deformable member may be attached to a connecting surface of the housing located inside the recess and may substantially extend along the longitudinal direction and in the distal direction. That means the deformable member may extend from the connecting surface perpendicular to the insertion direction of the cartridge, which is along the longitudinal direction. The term "substantially" means that the connecting surface may not exactly be orientated in the longitudinal direction but may be orientated from about $-10°$ to $+10°$ different from the longitudinal direction.

The proximal end of the deformable member may be attached to the connecting surface on the sidewall of the recess and may not be arranged in the space filled by the inserted cartridge. If the cartridge is inserted deeper into the recess than the final axial end position, then the deformable member may be deflected and the arch may be further deformed but the movement of the cartridge may not be blocked by the deformable member.

For instance, the cartridge, if further moved into the housing, may abut an axial end stop element inside the housing, which may be separated from the deformable member. Since the deformable member may be attached to a surface extending along the longitudinal direction or to a sidewall of the recess, the resisting force of the deformable member may increase only to a specific maximum value. Hence, the cartridge may not be damaged or broken by the deformable member because the force acting on the cartridge cannot exceed the maximum value or a predefined threshold.

In contrast, a spring or any deformable element which may be attached to a connecting surface perpendicular to the longitudinal direction (and thus perpendicular to the movement of an inserting cartridge) or a deformable element which is arranged on a proximal front end side of the inserted cartridge may only be deformed to a specific maximum and the resisting force caused by the element may abruptly increase to a breaking force when the cartridge is inserted too deeply into the recess.

According to certain implementations, the connecting surface may be an outer wall of an element inside the recess of the housing.

Such an outer wall may be, for example, an outer surface of an insert element arranged coaxially inside the recess, where the outer wall of the insert extends along the longitudinal direction. In this case, the deformable member may extend preferably radially outward from the outer wall in the direction to the inner sidewall of the recess.

In an alternative embodiment the connecting surface may be an inner sidewall of the recess. In this case, the deformable member(s) may extend radially inward from the inner sidewall to a center of the recess.

The housing may include a stop element adapted to prevent a movement of the cartridge in the longitudinal direction beyond the stop element. The stop element may be separate from the deformable member. That means the stop element may not be a part or a portion of the deformable member. The stop element may be unitarily formed with the housing or it may be a separate element connectable to the housing.

The stop element may be adapted to stop or block any movement of the cartridge in the proximal and longitudinal direction. In contrast, the deformable member may be adapted to limit a movement of the cartridge in the proximal and longitudinal direction, which means a movement may not be prevented per se, but may be restricted and may be dependent on forces acting on the cartridge in the longitudinal direction.

Since the stop element is separated from the deformable member the two may separately function to limit a movement (and/or bias the cartridge) and provide an axial end stop. This may enable each function to be carried out optimally. For instance, the deformable member may be configured such that the resisting force or holding force (caused by the deformed member) in relation of the deflection of the deformable member may be adjusted to a specific cartridge length or range of lengths. Additionally, a stop end adapted to block a proximal movement of the cartridge inside the housing beyond a specific axial position may be provided independent of the deformable member in a space-saving design.

Implementations further relate to providing a cartridge unit including a housing as described herein, the cartridge containing the liquid drug, a cartridge holder for accommodating a distal portion of the cartridge and connectable to a distal end of the housing such that the cartridge may be held relative to the housing by the cartridge holder and the housing. The deformable member may be deformable from the non-deformed state to the deformed state by a displacement of the distal end of the deformable member. The displacement may be caused by an insertion of a proximal portion of the cartridge into the housing, for instance where a proximal end of the cartridge abuts the distal end of the deformable member. Therefore, in the deformed state the proximal end of the cartridge may abut the distal end of the deformable member.

In an assembled state, the distal portion of the cartridge may be within the cartridge holder and the proximal portion of the cartridge may be within the housing. Furthermore, a proximal end of the cartridge holder may be connected to a distal end of the housing. Thus, the cartridge may be held within the cartridge holder and the housing because the deformable member may be in the deformed state and the deformed deformable member may limit a movement of the cartridge relative to the housing and the cartridge holder.

Further implementations provide a drug delivery device for administrating a liquid drug from the cartridge comprising the cartridge unit as described previously, and a dosing and dispensing mechanism.

Methods for assembling a cartridge unit for a drug delivery device are also provided, and may involve the steps of:

a. Providing a housing including a recess for accommodating a proximal portion of the cartridge, the recess having an axis defining a longitudinal direction, a deformable member being arranged inside the recess, where the deformable member includes a proximal end attached to the housing and a distal end movable within the recess relative to the housing, the deformable member further including an arch;

b. Inserting a distal portion of the cartridge into an opening of a sleeve-shaped cartridge holder;

c. Inserting a proximal end portion of the cartridge holder with the cartridge into the recess of the housing in the longitudinal direction;

d. Deforming, by a proximal end of the cartridge, the deformable member of the housing from a non-deformed state to a deformed state by a displacement of a distal end of the deformable member in the proximal and longitudinal direction and thereby deforming the arch both elastically and plastically;

e. Connecting the proximal end portion of the cartridge holder with a distal end portion of the housing, in particular by a snap lock.

The cartridge may be firstly inserted with its distal portion into the opening of the cartridge holder and secondly the cartridge holder with the inserted cartridge can be connected with the proximal end of the cartridge holder to the housing. Alternatively, the cartridge can be firstly inserted with its proximal portion into the opening of the housing and secondly the cartridge holder can be pulled over the distal portion of the cartridge and thirdly the proximal end of the cartridge holder can be connected to the housing.

BRIEF DESCRIPTION OF THE DRAWINGS

The subject matter of the present disclosure will be explained in more detail in the following text with reference to the disclosed embodiments, which are illustrated in the attached drawings, in which.

The reference symbols used in the drawings, and their primary meanings, are listed in summary form in the list of designations. In principle, identical parts are provided with the same reference symbols in the figures.

DETAILED DESCRIPTION

Figure 1:
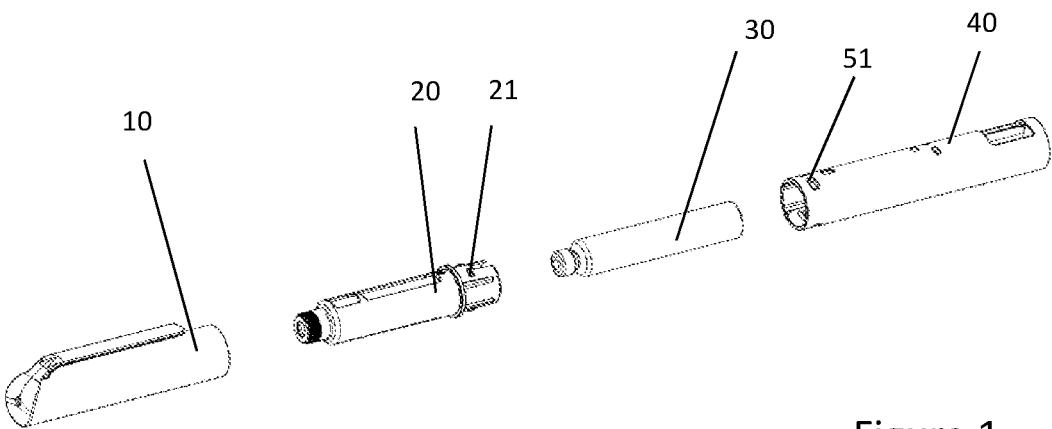
FIG. 1 depicts an isometric view of an injection pen that may be used in connection with implementations of the present disclosure.

The following describes a drug delivery device with a cartridge unit and a housing according to the present disclosure. The drug delivery device may be in the form of an injection pen, as described herein. FIG. 1 shows an isometric view of certain components of the injection pen, namely a housing 40, a cartridge 30, a cartridge holder 20 and a pen cap 10. The injection pen may further include a dosing and dispensing mechanism. The housing 40, the cartridge 30 and the cartridge holder 20 may form a cartridge unit. In the following disclosure, the cartridge unit is described in detail. Firstly, the structural features are described, and secondly, the functional features are depicted in detail.

Figure 2A:
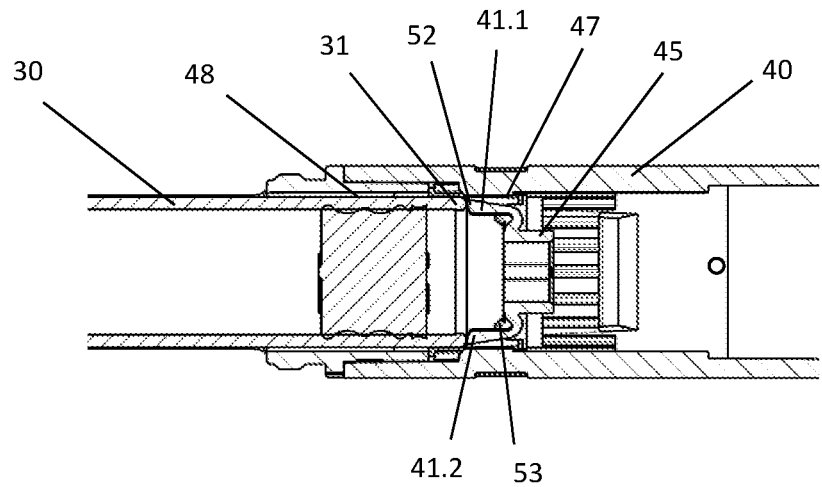
FIG. 2a depicts a cross-sectional view of an injection pen assembly including components of FIG. 1 taken along the longitudinal axis of the injection pen housing, according to implementations of the present disclosure.

FIG. 2a depicts a cross-sectional view of the cartridge unit, where the cross-sectional view is taken along the longitudinal axis of the housing 40. The housing 40 is illustrated as having a sleeve shape and may be made of polypropylene. In a proximal portion of the housing 40, a dosing and dispensing mechanism may be accommodated. The housing 40 may include a recess 48 at a distal end portion, which recess 48 may be adapted to accommodate a proximal portion of the cartridge 30. The recess 48 may have a substantially cylindrical shape. An opening forms a distal end of the recess 48 while a bottom portion may be made of four struts 49 circumferentially spaced apart from each other (see FIG. 2*b*) and may form the proximal end of the recess 48. The struts 49 may support an insert 45 with a through hole in the center of the recess 48. The through hole may serve as a guide for an axially moveable piston rod of the dosing and dispensing mechanism. An axis extending from the distal end to the proximal end of the recess 48 defines a longitudinal direction.

Figure 2B:
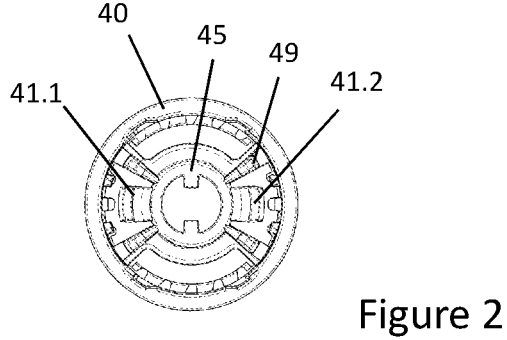
FIG. 2b depicts a front view of the housing of the injection pen assembly of FIG. 2a, without cartridge and cartridge holder.

As shown in FIGS. 2*a* and 2*b* two deformable members in the form of arms 41.1, 41.2 are attached to an outer circumferential wall of the insert 45. The two arms 41.1, 41.2 may be circumferentially spaced apart from each other. A distal end 52 of each arm 41.1, 41.2 may be moveable within the recess 48 relative to the housing 40 and a proximal end of each arm 41.1, 41.2 may be inextricably (e.g., non-removably) attached to the outer wall 46 of the insert 45, e.g., may be integrally formed therewith. Each arm 41.1, 41.2 may include a first arch 42 and a second arch 43 (see FIGS. 3*a*-3*d*) which may be arranged such that the arm has an s-shape. Starting from the attached proximal end of the arm, the arm 41.1, 41.2 may include a bend or curve by the first arch 42 from the wall of the insert 45 in the proximal direction. The second arch 43 may be adjacent the first arch and thus the arm 41.1, 41.2 may have a bend or curve back in the distal direction by the second arch 43. Each arm 41.1, 41.2 may further include a straight section 44 at a distal portion of the arm 41.1, 41.2. In FIGS. 2*a* and 2*b*, the straight section 44 extends substantially along the longitudinal direction. The straight section 44 may include a rib on its outer side such that the cross-section of the straight section is not rectangular. The distal end 52 of the arm may be moveable relative to an inner sidewall of the recess 48.

The plane area of the cross-section of each arm 41.1, 41.2 may vary between the distal end and the proximal end of the arm. Namely, the plane area of the cross-section may decrease from the distal end of the arm 41.1, 41.2 to the arches 42, 43 of the arm such that the plane area of the cross-section in the s-shaped portion may be reduced compared to the plane area of the cross-section in a distal portion of the arm 41.1, 41.2.

On an inner sidewall of the recess 48 two sliding surfaces 47 may be arranged along the longitudinal direction and circumferentially spaced apart from each other such that the sliding surfaces 47 are next to the distal end 52 of each arm 41.1, 41.2.

The housing 40 may further include an end stop 53, which may stop or block a proximal movement of the cartridge 30 beyond an end stop position. The end stop 53 may include a stop surface that is arranged perpendicular to an insertion direction and which may be arranged on each strut 49 at the bottom of the recess 48. When the cartridge is moved proximally beyond its final axial position it abuts the end stop 53 after a short movement in the proximal direction. Hence, the end stop 53 may prevent further insertion in the proximal direction.

The cartridge holder 20 as shown in FIG. 1 may be sleeve-shaped and may also include a recess, but may be adapted to accommodate a distal portion of the cartridge 30. The cartridge holder 20 may include latches or hooks 21 at its proximal end, which may be configured to engage with apertures 51 or counter elements arranged on a distal end of the housing 40. In the embodiment shown, the cartridge holder 20 may be connected with its proximal end to the distal end of the housing 40 by a snap lock connection. Alternatively, the cartridge holder 20 may be connected with the housing 40 by any other connecting means, for example, by adhesive bonding, by plastic welding, by a thread or by a bayonet fitting.

The function of the deformable arms 41.1, 41.2 and the interaction of the cartridge 30 with the housing 40 and the cartridge holder 20 is described in the following with reference to FIGS. 3*a* to 3*d*.

Figures 3A, 3B, 3C, 3D:
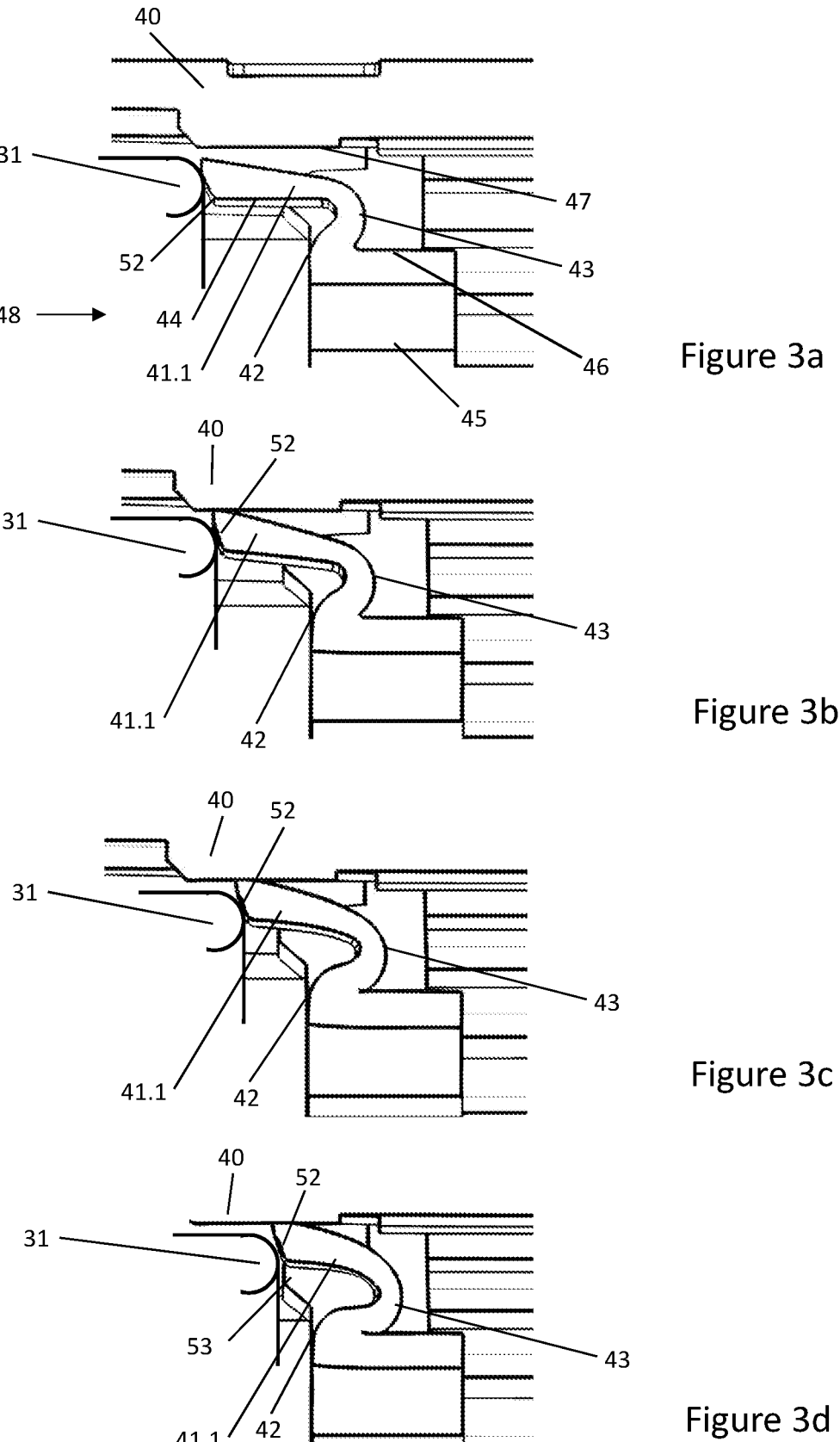
FIGS. 3a, 3b, 3c, and 3d depict cross-sectional views of the deformable member as the deformable member moves from the non-deformed to the deformed state, according to implementations of the present disclosure.

FIGS. 3*a* to 3*d* show a cross-sectional, detailed view of the deformable arms 41.1, 41.2 of the housing 40. The cross-sectional view runs along the longitudinal direction of the housing 40 and shows only the upper part of the cross-section. In FIG. 3*a*, an initial and non-deformed state of the deformable arms 41.1, 41.2 is depicted. When the cartridge 30 is inserted into the recess 48 via its proximal portion, a proximal end or rim portion 31 of the cartridge 30 abuts a distal end 52 of the arms 41.1, 41.2. If the cartridge 30 is further inserted in proximal and in the longitudinal direction into the recess 48 of the housing 40 the rim portion 31 of the cartridge 30 moves the distal end 52 of the arm 41.1, 41.2 radially outward on a sliding surface 47 and slightly moves the distal end 52 in proximal direction, as shown in FIG. 3*b*. Consequently, an outer distal edge of the arm 41.1, 41.2 abuts the sliding surface 47 on the inner sidewall of the recess 48 and the distal end 52 of each arm 41.1, 41.2 is further moved in the proximal direction sliding along the surface 47. This movement deforms the two arches 42, 43 of each arm 41.1, 41.2. Due to the elastic deformation of the deformable material (e.g., polypropylene) of the arms 41.1, 41.2 at this stage, a reaction force or resisting force is caused by the deformation. The reaction force or resisting force acts on the rim portion 31 of the cartridge 30 and is substantially directed in the distal direction.

Further insertion of the cartridge 30 in the proximal direction moves the distal ends 52 of the arms 41.1, 41.2 further along the sliding surface 47 of the sidewall of the recess 48 in the proximal direction and thereby further deforming the arches 42, 43 of each arm 41.1, 41.2. In particular, the first arch 42 is bent towards a center line or center of the recess 48. Due to that movement at least one of the two arches 42, 43 is deformed plastically. That means the deformation is irreversible and the deformation stays even after removal of the applied force by the cartridge insertion. From this instant, the arms 41.1, 41.2 are in the deformed state. That means in the deformed state the deformation of the material goes beyond a pure linear elastic deformation.

The position of the arms 41.1, 41.2 after the further insertion of the cartridge 30 in proximal direction is shown in FIG. 3*c*. At this stage, the first and the second arch 42, 43 are significantly deformed. The first arch 42 is bent or pressed towards a rigid outer wall 46 of the insert 45, whereas the second arch 43 is widened or stretched.

FIG. 3*d* shows the final inserted position of the cartridge 30. The first and second arch 42, 43 of the arms 41.1, 41.2 are even more deformed than in the previous position shown in FIGS. 3*a* to 3*c*. The deformation of the arms 41.1, 41.2 is still elastic and plastic, and the arms 41.1, 41.2 are still in the deformed state. In case the cartridge 30 would be inserted even further into the recess in the longitudinal direction, the reaction force would only slightly increase to a maximal value. However, the reaction force cannot exceed the maximal value due to the s-shape of the arms 41.1, 41.2. That effect will be described in detail with respect to the force-deflection diagram of FIG. 4. In this final position, the rim portion 31 of the cartridge 30 is near the end stop 53 but does not yet abut the end stop 53.

After the cartridge 30 is inserted into the recess 48 of the housing 40 up to a predefined axial position (inserted end position) the cartridge holder 20 is snapped with its latches or hooks 21 at the proximal end with the apertures 51 at the distal end of the housing 40. The cartridge 30 may be either first inserted with its distal portion into the recess of the cartridge holder, and then the cartridge holder 20 with cartridge 30 may be connected to the housing 40, or the cartridge 30 may be first inserted with its proximal portion into the recess 48 of the housing 40 and then the cartridge holder 20 may be put over the distal end of the cartridge 30 and subsequently connected to the housing 40.

Figure 4:
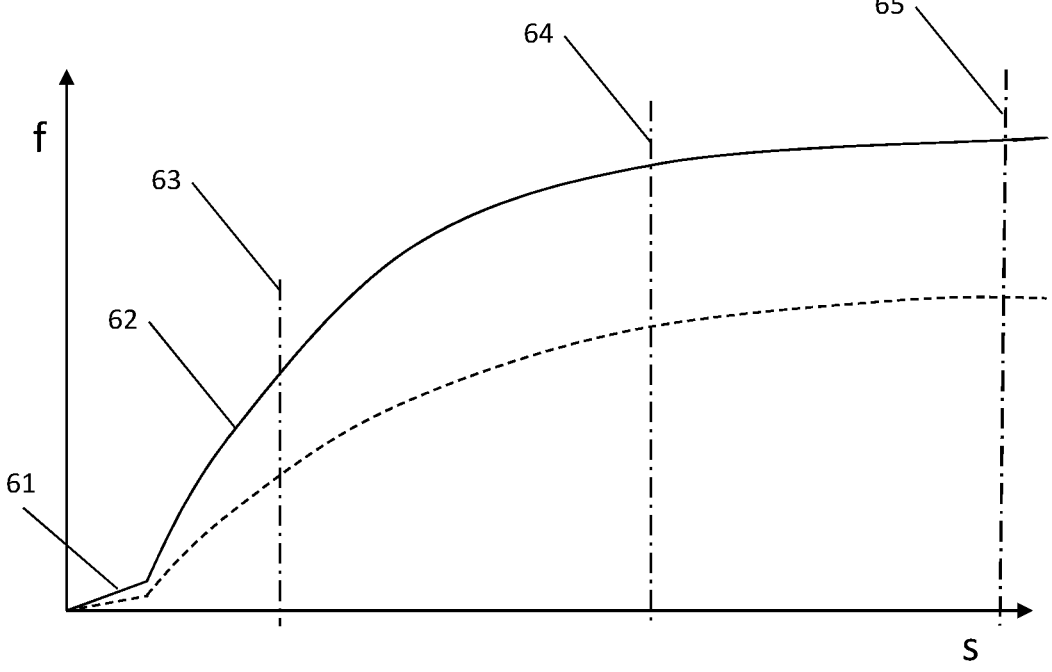
FIG. 4 depicts a diagram showing the force progression in relation to the deflection of the deformable member.

In FIG. 4 a force-deflection diagram is depicted, which shows the force progression of the reaction force (resistant force) of the arms 41.1, 41.2 in relation the deflection or deforming path of the arms (force vs. deflection).

The horizontal axis (labeled s-axis) shows the amount of deflection or the deformation path of the arms 41.1, 41.2 in the proximal and longitudinal direction when the distal end 52 of the arms 41.1, 41.2 is displaced from an initial distal position to a proximal position in the deformed state. The vertical axis (labeled f-axis) shows the force progression of the reaction force or resisting force of the arms 41.1, 41.2.

A first section 61 of the curve in the diagram is nearly linear. This is at the very beginning of the deformation when the arm is bent radially outward (corresponding to the deformation shown in FIG. 3b) and the material of the arms 41.1, 41.2 is then in its linear elastic region. Further deflection of the arms—only axial movement of the distal end 52 of the arm 41.1, 41.2 in proximal direction is possible— abruptly increases the force. The curve in the diagram has a sharp bend and subsequently the curve rises strongly in the second section 62 which is non-linear. From this point, the behavior is non-linear and not only an elastic but also a plastic deformation of the arms 41.1, 41.2 occurs at this stage. Thus, the arms 41.1, 41.2 have been transformed from the non-deformed state to the deformed state. That means at that stage the material is deformed not only elastically but also plastically.

Due to the arch-shaped arms the force-deflection curve has a predefined optimal procession. Namely, the maximal value of the force is chosen such that the cartridge is not damaged. Even if the cartridge is longer than expected or even if the cartridge is inserted too deeply into the housing the resisting force or reaction force acting on the cartridge does not exceed a predefined maximum value. That means the force-deflection curve is flattened or nearly horizontal at a greater deflection of the arms (see end section of the diagram).

The uninterrupted or solid line of the graph shows the behavior deflection vs. force in with new molded polypropylene material. The dotted line of the graph shows the behavior if the polypropylene material is stored for 100,000 hours. Due to the material relaxation the resistant force is lower than with new material. However, with the s-shaped arms disclosed herein, the resisting force is still above a required minimum force to bias the cartridge against the cartridge holder in order to reliably hold the cartridge within the cartridge holder and the housing.

The vertical lines 63, 64 and 65 define the deflection range used for holding the cartridge. The range is broad in order to cover cartridges with different lengths. The left vertical line 63 defines the lower end of the range or a lower threshold with a minimum deflection if a short cartridge is held. The force generated by the deformed arms is still high enough to bias the short cartridge against the cartridge holder to reliably and safely hold the cartridge within the cartridge holder and the housing. The vertical line 64 in the middle of the deflection axis marks the nominal value 64 of deflection. The right vertical line 65 defines the upper end of the deflection for longer cartridges. The force generated by the deformed arms if inserted a long cartridge does not exceed a predefined value and thus even a long cartridge cannot be damaged.

Figure 5:
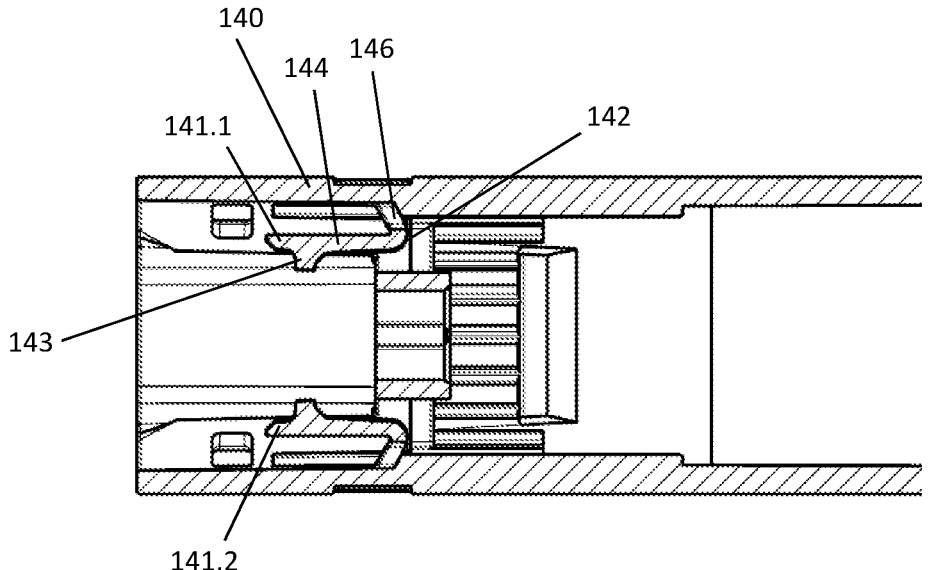
FIG. 5 depicts a cross-sectional view of a housing for a smaller cartridge taken along the longitudinal axils of an injection pen.

FIG. 5 depicts a sectional view of a further implementation of the present disclosure. The housing 140 shown in FIG. 5 is adapted for cartridges having a relatively smaller diameter, for example for a cartridge containing 1.5 ml of a drug, than the larger cartridges, for example for cartridges containing 3 ml of a drug, used for the housing 40 as described previously with reference to FIGS. 1 to 3.

In contrast to the previously described embodiments of FIGS. 1 to 3, the arms 141, e.g., 141.1, 141.2, are attached to an inner wall of the recess and not to the insert of the housing 140. Furthermore, the arms 141 may include only one arch 142. The proximal end of the arm may be attached to the inner wall of the recess and a first proximal section 146 of the arm 141 may extend inclined in a proximal direction. The arch 142 may follow the proximal section 146 such that a distal and straight section 144 of the arm 141 may points in a distal direction. The straight section 144 of the arm 141 may include a radially inwardly directed ledge 143, which may be adapted to support the rim portion 31 of the inserted cartridge.

The insertion of a cartridge into the housing 140 and the deformation of the arms 141 corresponds to the embodiment described previously with reference to FIGS. 1 to 3. Namely, when inserting a cartridge the proximal end or rim portion of the cartridge abuts the ledge 143. Further insertion of the cartridge moves the distal end of the arms 141 in the proximal direction. This leads to a deformation of the arches 142 and the arms 141 are deformed from the non-deformed state to the deformed state as described previously with respect to the first embodiment.

While the embodiments have been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims does not indicate that a combination of these elements or steps cannot be used to advantage, specifically, in addition to the actual claim dependency, any further meaningful claim combination shall be considered disclosed.

LIST OF DESIGNATIONS

10 cap
20 cartridge holder
21 latch element
30 cartridge
31 rim portion
40 housing
41.1, 41.2 arms
42 first arch
43 second arch
44 straight section
45 insert
46 outer wall of insert 47 sliding surface
48 recess
49 struts
51 apertures
52 distal end
53 end stop
61 linear section
62 non-linear section
63 left vertical line
64 nominal value line
65 right vertical line
140 housing
141.1, 141.2 arm
142 arch
143 ledge
144 straight section
146 proximal end section

What is claimed is:

1. A housing for a drug delivery device for administrating a liquid drug from a cartridge, the housing comprising:
    a recess for accommodating a proximal portion of the cartridge, the recess having an axis defining a longitudinal direction; and
    a deformable member arranged inside of the recess, wherein the deformable member is formed in one piece and comprises a proximal end attached to the housing and a distal end movable within the recess relative to the housing,
    wherein the deformable member is deformable from a non-deformed state to a deformed state by a displacement of the distal end, wherein in the deformed state the deformable member is configured to limit a movement of a cartridge arranged in the recess in the longitudinal direction relative to the housing, and
    wherein the deformable member comprises an arch, and in the deformed state the arch is deformed both elastically and plastically.

2. The housing according to claim 1, wherein the deformable member is arm-shaped and wherein the arch is located between the proximal end and the distal end of the arm-shaped deformable member.

3. The housing according to claim 1, wherein the deformable member is deformable from the non-deformed state to the deformed state by a displacement of the distal end in the longitudinal direction relative to the housing.

4. The housing according to claim 1, wherein a distance between the proximal end and the distal end defines a length of the deformable member in the longitudinal direction, wherein in the deformed state, the length is reduced compared to the non-deformed state.

5. The housing according to claim 1, wherein in the deformed state a first portion of the arch is elongated and a second portion of the arch is compressed compared to the non-deformed state.

6. The housing according to claim 1, wherein the deformable member comprises a second arch, wherein the first arch and the second arch define a S-shaped form in the non-deformed state and in the deformed state.

7. The housing according to claim 1, wherein a plane area of the cross-section of the deformable member varies between the proximal end and the distal end.

8. The housing according to claim 1, wherein the deformable member is unitarily formed with the housing.

9. The housing according to claim 1, wherein the deformable member is made of a polymer selected from one or more of: polyoxymethylene, polypropylene, polyethylene, polycarbonate-acrylonitrile-butadiene-styrene, polybutylen-terephthalate, a polyester or a polyamide.

10. The housing according to claim 1, wherein the deformable member is a first deformable member, and further comprising a second deformable member arranged inside of the recess.

11. The housing according to claim 1, wherein the proximal end of the deformable member is attached to a surface of the housing located inside of the recess and substantially extends in the longitudinal direction.

12. The housing according to claim 11, wherein the surface is an outer wall of an insert element arranged coaxially inside of the recess of the housing.

13. The housing according to claim 11, wherein the housing comprises a stop element adapted to prevent a movement of the cartridge in the proximal direction beyond the stop element, wherein the stop element is separate from the deformable member.

14. A cartridge unit for a drug delivery device, the cartridge unit comprising:
    a housing, the housing comprising:
        a recess for accommodating a proximal portion of a cartridge containing a liquid drug, the recess having an axis defining a longitudinal direction; and
        a deformable member arranged inside of the recess, wherein the deformable member is formed in one piece and comprises a proximal end attached to the housing and a distal end movable within the recess relative to the housing,
        wherein the deformable member is deformable from a non-deformed state to a deformed state by a displacement of the distal end, wherein in the deformed state the deformable member is configured to limit a movement of the cartridge arranged in the recess in the longitudinal direction relative to the housing, and
        wherein the deformable member comprises an arch, and in the deformed state the arch is deformed both elastically and plastically by the cartridge; and
    a cartridge holder for accommodating a distal portion of the cartridge and connectable to a distal end of the housing such that the cartridge is held relative to the housing by the cartridge holder and the housing,
    wherein in the deformed state a proximal end of the cartridge abuts the distal end of the deformable member.

15. The cartridge unit of claim 14, wherein the cartridge unit is incorporated with the drug delivery device, the drug delivery device configured for administrating the liquid drug from the cartridge.

16. The cartridge unit of claim 15, wherein the drug delivery device comprises a dosing and dispensing mechanism.

17. A method for assembling a cartridge unit for a drug delivery device, comprising the steps of:
    obtaining a housing, the housing comprising a recess for accommodating a proximal portion of the cartridge, the recess having an axis defining a longitudinal direction, a deformable member being arranged inside the recess, wherein the deformable member is formed in one piece and includes a proximal end attached to the housing and a distal end movable within the recess relative to the housing, the deformable member further comprising an arch;
    inserting a distal portion of the cartridge into an opening of a sleeve-shaped cartridge holder;

inserting a proximal end portion of the cartridge holder
   containing the cartridge into the recess of the housing
   in the longitudinal direction;
deforming, using a proximal end of the cartridge, the
   deformable member of the housing from a non-deformed state to a deformed state by a displacement of
   a distal end of the deformable member in the proximal
   and longitudinal direction to thereby deform the arch
   both elastically and plastically; and
connecting the proximal end portion of the cartridge
holder with a distal end portion of the housing.

18. The method of claim 17, wherein the step of connect-
ing the proximal end portion to the distal end portion is via
a snap lock.

19. The method of claim 17, wherein the cartridge is
firstly inserted into the cartridge holder and secondly the
cartridge holder with the inserted cartridge is connected via
the proximal end of the cartridge holder to the housing, or
wherein the proximal end of the cartridge is firstly inserted
into the opening of the recess of the housing and secondly
the cartridge is inserted into the cartridge holder and thirdly
the proximal end of the cartridge holder is connected to the
housing.

* * * * *